US006626537B1

United States Patent
Odom et al.

(10) Patent No.: US 6,626,537 B1
(45) Date of Patent: Sep. 30, 2003

(54) NON-INVASIVE OCULAR DYNAMIC MONITORING ASSESSMENT METHOD AND ASSOCIATED APPARATUS

(75) Inventors: James Odom, Morgantown, WV (US); James Smith, Bruceton Mills, WV (US); Robert Craven, Morgantown, WV (US); Ahmed El-Sherbeeny, Morgantown, WV (US)

(73) Assignee: West Virginia University, Morgantown, WV (US)

( * ) Notice: Subject to any disclaimer, the term of this patent is extended or adjusted under 35 U.S.C. 154(b) by 0 days.

(21) Appl. No.: 09/860,241

(22) Filed: May 18, 2001

(51) Int. Cl.[7] .................................................. A61B 3/10
(52) U.S. Cl. ........................ 351/205; 351/246; 600/318
(58) Field of Search .................................. 351/200, 205, 351/206, 209, 210, 213, 221, 246; 600/407, 318, 319, 320, 321, 558; 180/272; 340/500, 576

(56) References Cited

U.S. PATENT DOCUMENTS

| | | | | |
|---|---|---|---|---|
| 4,334,738 A | * | 6/1982 | Seckinger | 351/205 |
| 4,995,716 A | | 2/1991 | Warnicki et al. | |
| 5,129,400 A | * | 7/1992 | Makino et al. | 351/206 |
| 5,159,361 A | | 10/1992 | Cambier et al. | |
| 5,297,554 A | * | 3/1994 | Glynn et al. | 351/206 |
| 5,308,919 A | * | 5/1994 | Minnich | 351/221 |
| 5,422,690 A | * | 6/1995 | Rothberg et al. | 351/209 |
| 5,495,429 A | | 2/1996 | Craven et al. | |
| 5,666,953 A | * | 9/1997 | Wilk | 600/407 |
| 5,684,561 A | * | 11/1997 | Yancey | 351/209 |
| 5,729,619 A | * | 3/1998 | Puma | 382/115 |
| 6,056,424 A | | 5/2000 | DiNunzio | |
| 6,120,460 A | * | 9/2000 | Abreu | 600/558 |
| 6,285,505 B1 | * | 9/2001 | Melville et al. | 351/206 |
| 6,442,410 B1 | * | 8/2002 | Steffes | 600/319 |
| 2002/0024633 A1 | * | 2/2002 | Kim et al. | 351/206 |

* cited by examiner

Primary Examiner—Marvin M. Lateef
Assistant Examiner—John R. Sanders
(74) Attorney, Agent, or Firm—Arnold B. Silverman; Kirk D. Houser; Eckert Seamans Cherin & Mellott, LLC

(57) ABSTRACT

A method of monitoring a subject for medical conditions includes causing light to impinge on at least one eye of the subject, directing reflected light from such light beam to photosensors, converting the received reflected light to corresponding electrical signals which are delivered to a processor. Processing the signals by effecting a comparison between stored information regarding the medical condition and the data provided by the monitoring to determine if an undesired medical condition exists and, if so, communicating such result. The cycle is repeated at predetermined intervals which may be short or prolonged. The method may be employed for a wide variety of medical conditions and preferably is employed with frequent cyclic monitoring for conditions such as miosis, carbon monoxide poisoning, and blood flow related conditions. A related apparatus is provided.

31 Claims, 7 Drawing Sheets

NON-INVASIVE OCULAR DYNAMIC MONITORING ASSESSMENT METHOD AND ASSOCIATED APPARATUS

BACKGROUND OF THE INVENTION

1. Field of the Invention

The present invention relates to a method of dynamic monitoring of the eye to determine on an essentially real time basis certain physical conditions in the body and to apparatus for effecting such monitoring.

2. Description of the Prior Art

It has long been known to examine the eye to determine certain characteristics of the eye, such as near and far vision in order to ascertain whether an individual might need to wear corrective lenses in the form of eyeglasses or contact lenses, for example.

It has also been known to monitor the eye to determine other physical characteristics of the eye, such as the shape of the cornea. See, for example, U.S. Pat. No. 4,995,716 and 5,159,361.

U.S. Pat. No. 4,995,716 discloses apparatus for measuring the topography of a cornea. Light projection means projects a grid pattern on the eye which is coated with a substance capable of making the eye non-transparent. An electronic camera is provided in a second pathway in line with the eye for obtaining and producing an image of the grid pattern projected onto the eye. One arm of the apparatus carries the light projection means and the grid means on one side of the centerline and the camera means on the other side. Processing means are connected to the camera for obtaining data from the image of the grid pattern projected onto the eye thereby producing quantitative and qualitative analysis of the contour of the cornea. See, also, U.S. Pat. No. 5,159,361.

In summary, it has been known to provide apparatus to which non-contacting optical and electronic apparatus can make certain determinations about the eye itself as well as other conditions in the body as a result of changes in the eye.

In spite of the foregoing, there remains a real and substantial need for a method and associated apparatus for effecting generally real-time determinations regarding certain specific conditions in the body based upon examination of the eye.

SUMMARY OF THE INVENTION

The present invention has met the above-described needs.

The present invention has provided a method of monitoring a medical condition in a subject. The method includes impinging light on to the subject's eye and directing the reflected light from the impinging light beam to a photosensor with subsequent conversion in the photosensor of the reflected light into corresponding electrical signals. The electrical signals, are delivered to a processor, which may be a computer, which contains stored information regarding desired parameters of the particular medical condition. A comparison is effected between the photosensor delivered electrical signal containing the data and the stored data to determine if an undesirable medical condition exists and, if such an undesirable medical condition exists, communicating such event. The process is repeated cyclically. Among the specific conditions that may be monitored is miosis, carbon monoxide and other toxin levels in the body, and blood flow characteristics, for example.

The apparatus for monitoring a medical condition may have a light source directing light into at least one eye of the subject with sensor means for receiving the reflected light and converting light into corresponding electrical signals. Processor means receive the electrical signals and compare the same with stored information regarding desired parameters of the medical condition and emits the result of the comparison. The processor has controls for cyclically repeating the monitoring at desired predetermined intervals.

It is an object of the present invention to provide an efficient and accurate means of employing information obtained from the eye to determine whether certain changes in the physical condition of an individual have occurred.

It is a further object of the present invention to effect such determinations rapidly in minimum time.

It is yet another object of the present invention to provide apparatus for making such determinations in vehicles, customized head mounted apparel at workstations and other ways which facilitate ongoing monitoring of the eye without interfering meaningfully with activities of the individual being monitored.

It is yet a further object of the present invention to provide such a method and apparatus which employs computerized processing through comparison of the data obtained from observations of the eye with either prior data obtained from the same individual or standardized data regarding normal and/or abnormal conditions in the body.

It is another object of the invention to provide an automated system for continuous or intermittent monitoring of some optically apparent characteristic that corresponds to an undesirable metabolic state or to a toxic exposure.

It is yet another object of the present invention to provide a system which serves as an early warning or generalized information leading to subsequent medical analysis.

It is yet another object of the invention to provide such a system which permits frequent monitoring of certain medical conditions as determined from external observation of the eye in order to minimize safety and health risks.

These and other objects of the invention will be more fully understood from the following description of the invention with reference to the drawings appended hereto.

DESCRIPTION OF THE PREFERRED EMBODIMENTS

As employed herein, the term "subject" refers to human beings and other members of the animal kingdom unless in a specific usage an express indication to the contrary is provided.

As employed herein, "medical condition" means a condition of the body (other than direct measurement of vision) which condition can be determined through (a) monitoring of the condition of the eye or portions thereof or (b) changes in the condition of the eye or portions thereof and shall expressly include, but not be limited to miosis, blood monitoring, carbon monoxide monitoring, blood toxins, CN, heavy metals such as Ag, Hg, Pb, U; organophosphates, anticholinesterose, nerve gases, mental stress, and internal ocular conditions.

As employed herein, the term "head mounted apparel" shall include, but not be limited to, head mounted apparel containing all or a portion of the system of the present invention and shall expressly include deep sea diver helmets, head mounted apparel worn by drivers of vehicles, airplane pilot's headgear, skiers helmets, industrial safety headgear, and headgear worn in other types of sporting activities and events.

The health and function of the eye reflects the general health of the body. The neural retina and optic nerve are extensions of the central nervous system. As a result, agents, which have general neurotoxic effects, will often affect the retina and optic nerve as well. The eye is supplied with blood by the ocular vasculature, which are visible through the front of the eye. Generalized diseases that affect the cardiovascular system are reflected in changes in these ocular vessels. Fluids in the eye interact with the lymphatic system of the body. Many chemicals and metals which enter the body, are transported by the vascular or lymphatic systems are deposited in the eye. The cornea is an extremely sensitive ectodermal tissue that is sensitive to many of the same agents that affect the skin.

The method and apparatus of the present invention may be used in conjunction with a "dye" or other chemical injected into the blood stream or applied to the surface of the eye or its surrounding tissues. This dye or chemical might then react with a toxin and fluoresce or change color. The changes in the dye in time through the blood stream or on the surface of the eye or tissue surrounding the eye could provide indications of the presence of toxins or the health of vasculature and tissue or the accumulation of chemicals on or in vessels or tissues. Examples of this include, but are not limited to, current uses of fluorescein or other chemicals applied to the surface of the eye or orbit or injected to reveal vessels of the eye, retina, pupil and other ocular tissues. The system might monitor these changes statically or dynamically on the externally visible portions of the eye and its surrounding tissues or within the eye.

Figure 1:
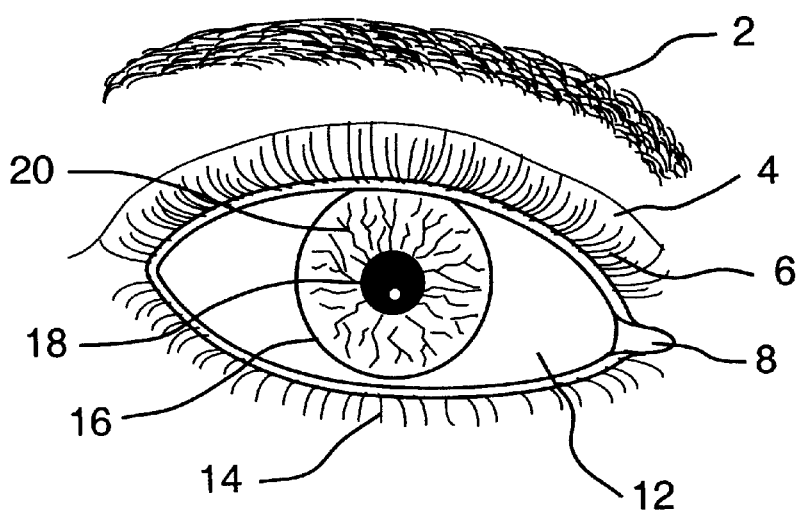
FIG. 1 is a schematic illustration of the human eye viewed from the exterior.

Referring to FIG. 1, there is shown an exterior view of a human eye which consists of an eyebrow 2, an upper eyelid 4, and eyelash 6 on the upper lid, a lacrimal duct 8, the white portion or sclera 12, a lower eyelid 14, an iris 16, a pupil 18, which is an opening in the iris 16, and the cornea 20.

Figure 2:
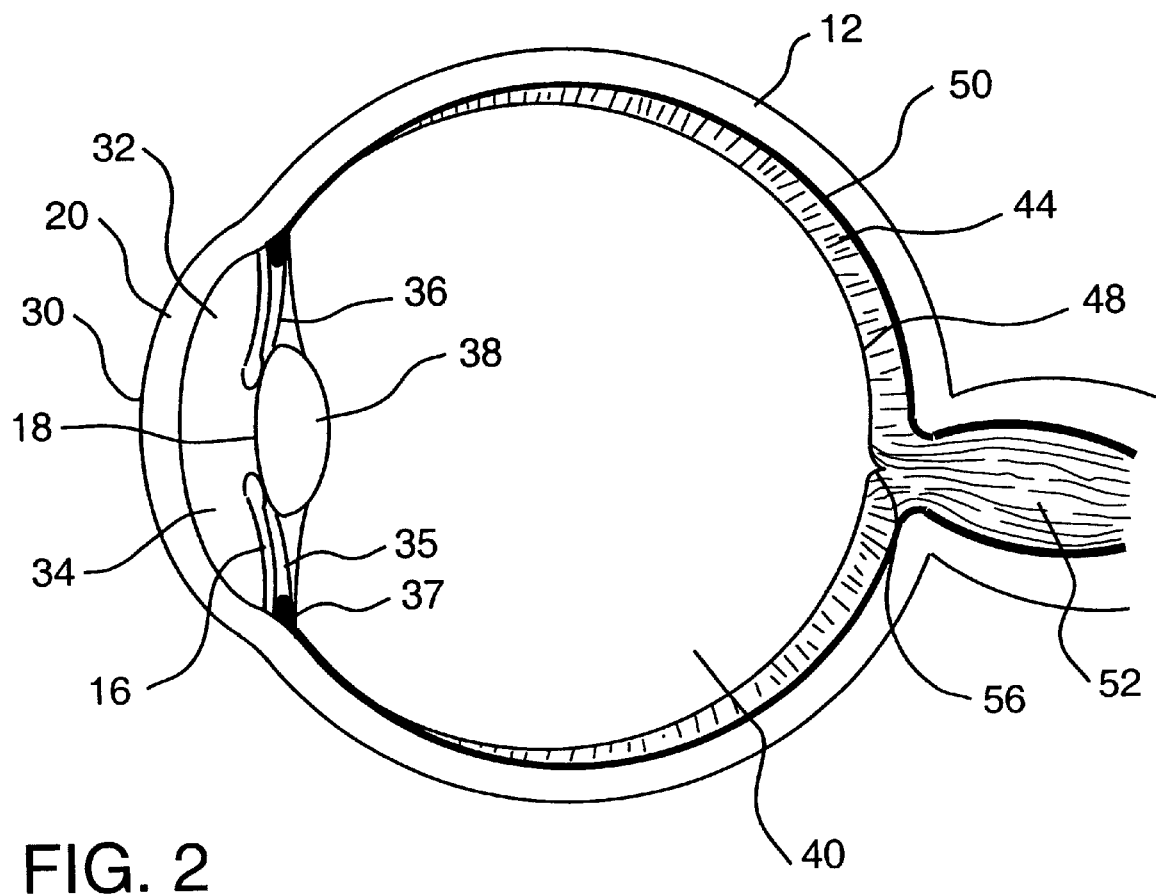
FIG. 2 is a schematic cross-section of the human eyeball.

FIG. 2 illustrates a cross-section of the human eyeball with the portion exposed to the exterior of the person appearing at the left where the conjunctiva 30 is located. An anterior chamber 32 and aqueous humor 34 are provided in the forefront. The suspensory ligament 36 is operatively associated with the lens 38. Other components of the eye are the vitreous body 40 which is disposed rearwardly of the lens 38 and forwardly of the retina 44 which has the fovea 48, optic nerve 52 and papilla 56 and choroid 50 positioned behind the same. The eye also contains the posterior chamber 35, the ciliary process 37 and the papilla 56. Light impinging upon the retina 44 in a particular pattern related to what the eye has observed is converted by the retina 44 into an electrical signal which is transmitted by the optic nerve 52 to the brain.

In one embodiment of this invention, measurement of miosis, which is constriction of the pupil to its minimum size or diameter, is effected. Miosis can be caused by the onset of sleep or intoxication from alcohol or a variety of drugs or exposure to neurotoxins or changes in light to which the eye is exposed. This system could be small, inexpensive and could be mounted on a head-mounted apparel such as a hat or helmet mounted in the dashboard of a vehicle. This device could also be applied to heads-up displays, sighting helmets and divers' facemasks or helmets. As such mounting arrangements are well known to those skilled in the art, they need not be provided herein in detail.

Another version of this system could be designed to measure relative natural light, pupil diameter and their co-variation and maintain some or all of these values in memory. Detection of changes in parameters, e.g., minimal or maximal pupillary diameter, variability of diameter or timing of pupil opening and closing relative to light would provide indications of the presence or type of neurotoxin present.

The invention preferably should be integrated into the subject's environment. Preferably, it would be integrated into a heads up display system, which while providing information to the subject would also permit monitoring of the subject's eye. Alternatively, the invention could be incorporated into the dashboard or visor or windshield of a vehicle with a zoomed view of the pilots/drivers eye.

Ambient illumination is preferred, but the heads up display could also serve as an illumination source. Alternatively, the system could be based on a non-visible wavelength of the electromagnetic spectrum, such as infrared viewing, either passively or actively illuminated.

An optics system would be employed for creating an image of the subject's eye on a sensor. Part of this system could be the light splitting system of a heads up display. The sensor is preferably a digital camera, but could be other types, such as video CCD cameras, CMOS devices, simple arrays of photo detectors, film, or others. The sensor can be selected to be sensitive to target portions of the light spectrum, however, simple gray scale cameras are probably adequate.

Filters can be utilized on the light beam reflected from the eye to further vary light spectrum selectivity. The miosis application does not require spectral measurements, but spectral filters may be utilized to minimize noise from the subject's environment or to filter out unwanted effects from the heads up display.

A processor for analyzing images, preferably a computer, but also including custom designed circuits may be employed. This also requires the appropriate means of conveying the image from the sensor into the processor. In one form, this could consist of a high-speed digital bus. The processor preferably segments the pupil from the whole image. These could be known segmentation algorithms or custom algorithms designed for pupil isolation. The processor may quantify pupil size and/or dynamic response. A comparison of size/dynamic response parameters to established norms may be made.

The results are then communicated which could include radioing distress signals, vibratory output, audible tones, visual indicators or automatic changes in the system being operated. Also, CRT displays, hard copy output and storage in the processor may be provided with or without computer enhancement.

Figure 3:
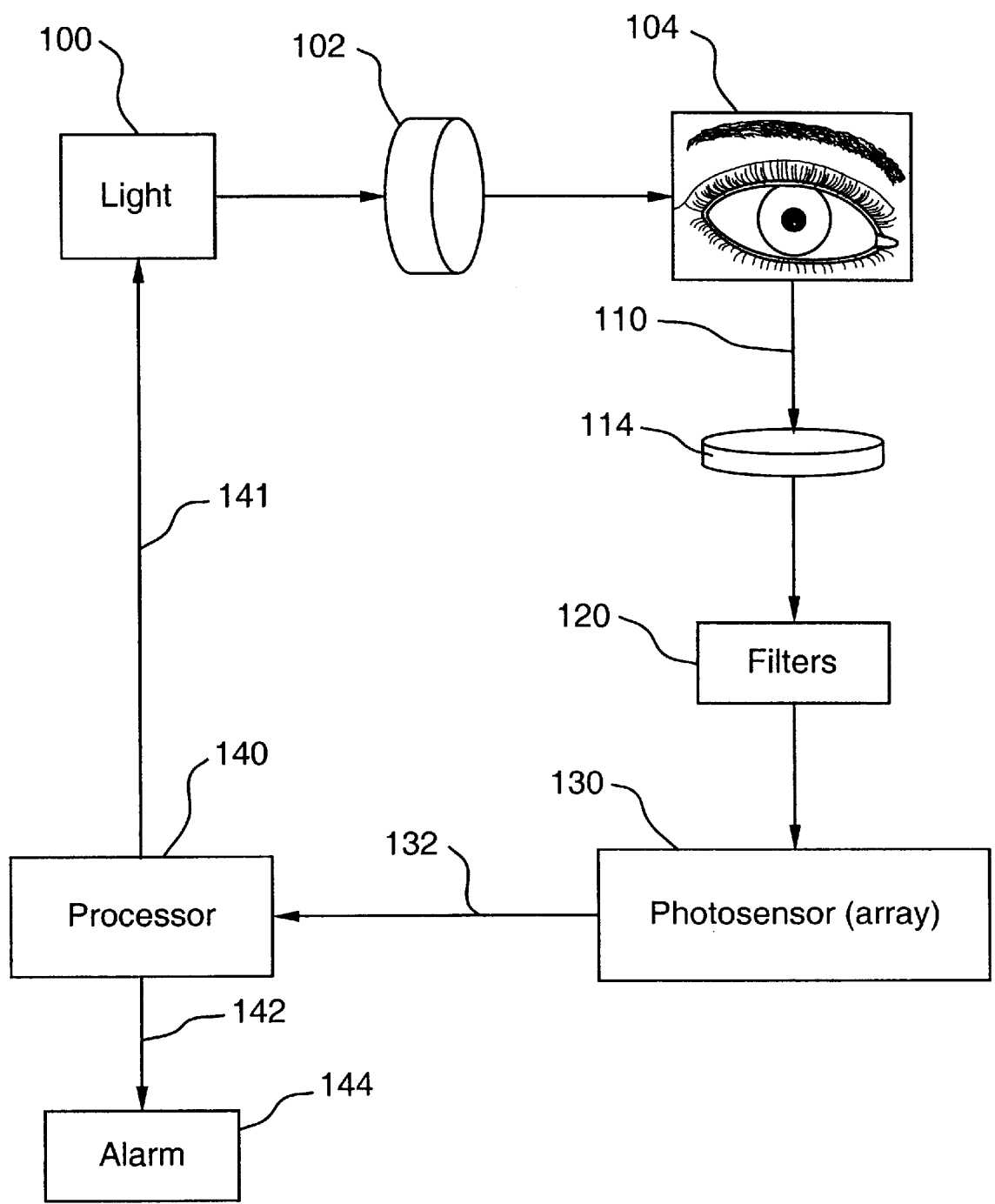
FIG. 3 is a flow diagram showing a method of monitoring miosis in an individual.

Referring now to FIG. 3, the form of apparatus employable in a miosis monitor of the present invention will be considered. This embodiment may be employed, for example, to warn of drowsiness. A light source 100, which may be infrared light, emits light through optics 102 which may be an appropriate lens or lens system, causes the light to impinge upon a subject's eye 104. The reflected light 110 passes through optics 114, which may be a lens or lens system, through filter 120 to a sensor or sensor array 130 which may, for example, be a camera or a self-scanning array of photodiodes responsive to the impinging light emits a corresponding electrical signal 132 to a processor 140 which may be any suitable processor programmed to process the data received. Processor 140 through lead 141 controls the frequency of cycle initiation by controlling light 100. In a preferred embodiment of the invention, the microprocessor 140, which may be a computer or an intelligent chip, will have stored therein a desired normal range of data which may either be that obtained from a general population source or in certain instances data obtained from the particular individual. When the data departs from the desired range by a predetermined amount, the processor 140 may, for example, emit a signal 142 to an alarm 144 which may take the form of an audible alarm, a visual alarm or a vibratory output which provides tactile feedback or a combination of these and other alarms so as to alert the individual being monitored or another to an undesired condition such as the onset of sleep or intoxication or reactions to drugs, including pharmaceutical and over-the-counter drugs, as well as illegal narcotics. This provides an opportunity for the individual to be spared from undesired consequences of one or more of these conditions.

Figure 4:
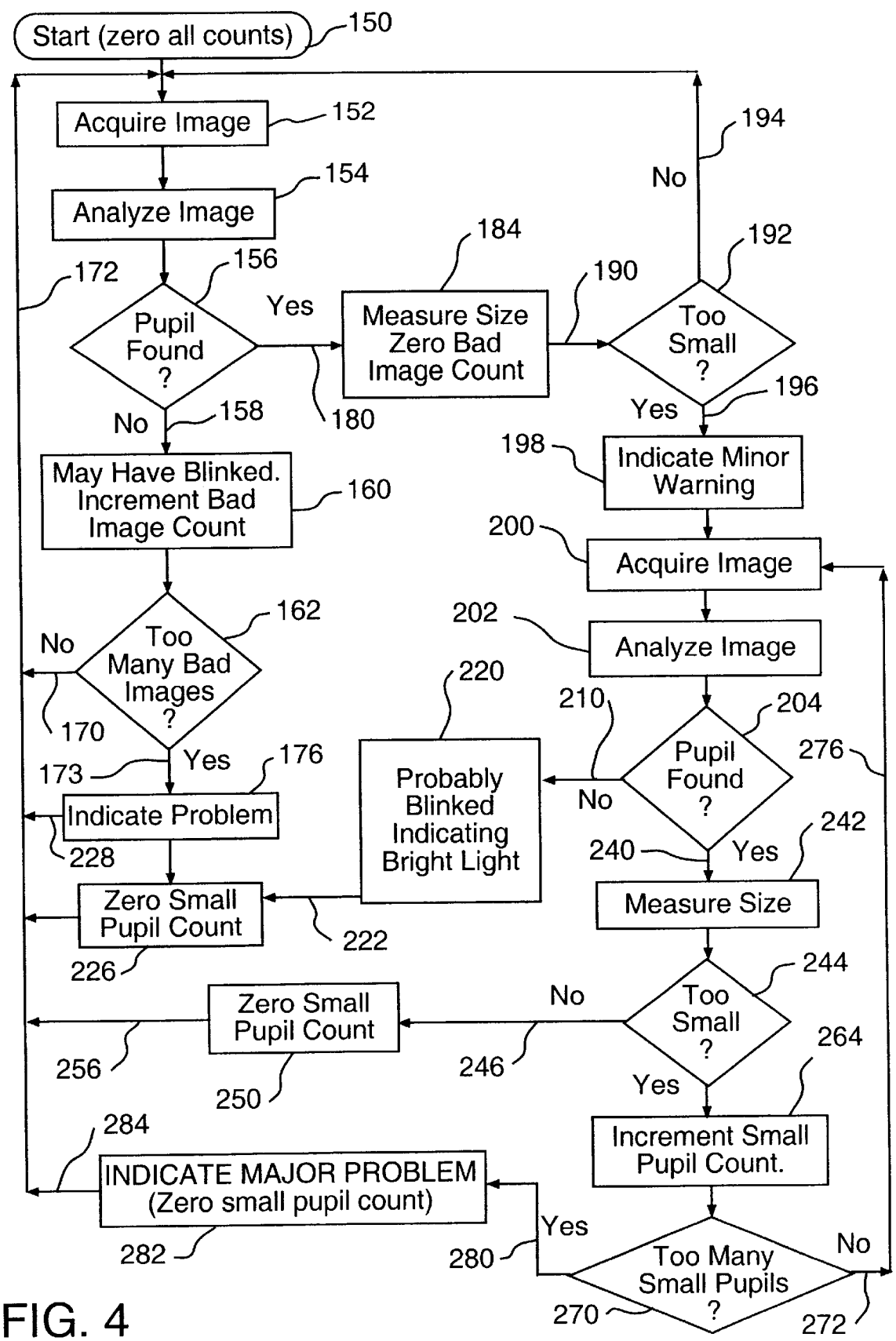
FIG. 4 is a more detailed flow diagram showing processor logic for a preferred method of miosis monitoring of the present invention.

Referring to FIG. 4, there is a flow chart illustrating a preferred method of miosis monitoring of the present invention. It will be appreciated that this monitoring is dynamic and essentially real time, if desired. By repeated cycles of monitoring at predetermined intervals, the method provides early warning of potential problems and facilitates timely corrective action.

The program logic begins by setting variables used for counting the number of bad images and the number of successive images where too small of a pupil was measured to zero 150. The program then starts a logic loop with the acquisition of an image 152. The analysis of that image to first find the pupil if present 154. A logic branch 156 chooses program flow along path 180 if there was a pupil found in the analysis 154 and along branch 158 if it was not. Along the path 180, a subsequent analysis is performed to determine the pupil size 184 with path 190 leading to a logic choice 192. A logic choice 192 is made depending on whether the pupil is too small 196 or acceptable 194. Most of the time, it is desired that the pupil size be not too small and that the loop starts all over at 152. The criterion for "too small" can either be based on statistics for "normalcy" for that particular individual or extrapolated from statistics of a larger sample pool.

If in the choice of too small 192, the pupil was determined to be too small 196, the program switches mode to a counting of time that this too small condition lasts. If it is of short duration, the change might have been caused by a bright light which momentarily reduced the pupil size. The minor warning 198 may not even be indicated or perhaps it will consist of entering a note in a recorder. The next step, therefore, in this alert mode is to again acquire an image 200, analyze at 202, detect a pupil and assess its size 204 and through path 240, if after measuring at 242 and assessing its size as too small 244, incrementally begin the counting variable associated with too small of a pupil count 264. (If pupil found 204 results in a "no" answer through path 210, probably blinked light 220 is illuminated and through path 222 the zero small pupil count 226 is indicated through path 172). If this heightened alert mode has gone on too long, as indicated by a large count 270, then a major problem needs to be indicated by path 280 at 282. If not, path 272 leads to acquire image 200. The major problem could result in a loud alarm, radio distress calls, engaging in autopilot or the like. If subsequent pupils are larger than the threshold 246, then the mode switches back to the normal program loop after first setting the small pupil count to zero 250 again, and delivering the information through paths 256, 172. In this way, only a series of time sequences, too small pupils, will trigger a major alert.

The remaining logic branch 158, 160, 162, 170, 173 176 and 228 is to handle the case when many sequential images have no pupil found. A few images with no pupil found could be explained by a single blink, but a large number could be the result of the individual being unconscious or for either reason there being an obstruction to viewing the pupil.

Excessive carbon monoxide (CO) within the body had been documented to cause a reddening of the conjunctiva of the eye. If there is a progression in this reddening with time and concentration of exposure, a monitoring system can provide early warning of CO exposure.

The present invention may also take advantage of the fact that may toxins have common bio-markers which tend to group together. For example, neuro-toxins tend to be similar to each other and heavy metals tend to be similar to each other. These characteristics serve to assist with the determination of relationships.

The invention is preferably integrated into the subject's environment. Preferably, it would be integrated into a heads up display system, which while providing information to the subject would also permit monitoring of the subject's eyes. Alternatively, the invention could be incorporated into the dashboard of a vehicle with a zoomed view of the pilot's/driver's eye. Ambient illumination is preferred, but the heads up display could also serve as an illumination source.

The preferred sensor is a system of two or three photosensors. The primary sensor should have optics gathering light for it from the sclera, or white of the eye, when the subject is looking in a prescribed direction (straight ahead, at a specific instrument or portion of a heads up display.) A second sensor could be utilized for measuring ambient light levels and associated measurement corrections. A third sensor could be positioned so that when the subject is looking in the prescribed direction (straight ahead), the low light reflectance corresponding to the dark pupil area of the eye could serve as a trigger to indicate that measurements of the white of the eye were valid.

Alternatively, the sensor could be the array of sensors of a digital camera where appropriate algorithms would determine where valid eye white measurements could be obtained. An algorithm for segmenting the sclera from a whole image could be a classic textbook segmentation algorithm or custom algorithms designed for pupil isolation.

Filters can be utilized to further vary light spectrum selectivity to the red portion of the spectrum.

A means for analyzing sensor data, preferably a custom circuit, but also including general microprocessors may be employed. This also requires the appropriate means of conveying the sensor data from the sensor into the processor. In a preferred embodiment, this would consist of a set of digitized voltages. The processor could be placed in close proximity to the sensor or, if desired, be remotely located with wired or wireless communication between the processor and sensors and related components.

A means of correcting the measurement for ambient light variations may be provided in the processor.

A means of establishing the sensor response to indicate acceptable or dangerous levels of CO exposure is provided.

A means of notifying someone of the results, could include radioing distress, audible tones for the subject, visual output, vibratory output or putting a vehicle into a "safe" mode of operation.

Figure 5:
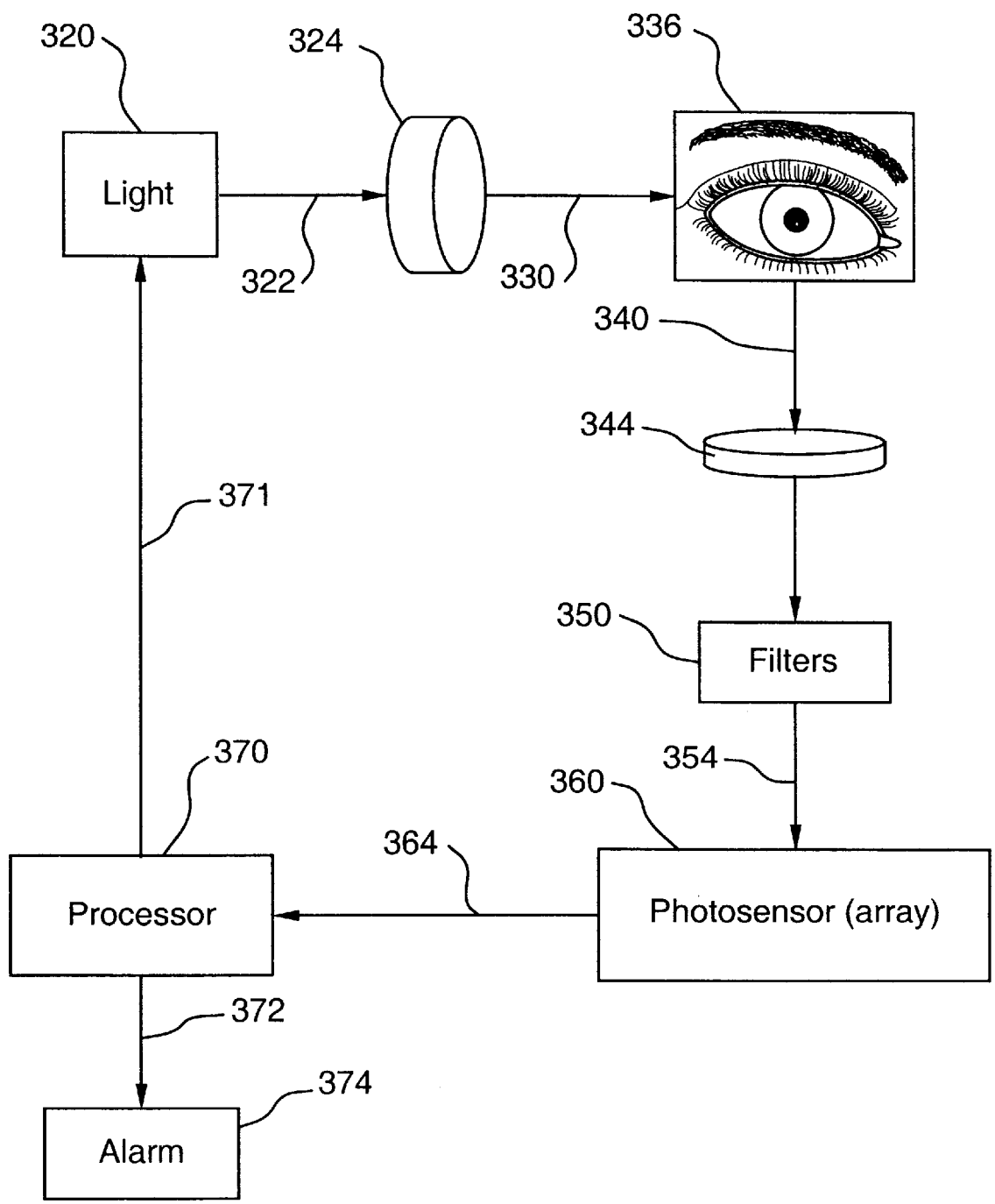
FIG. 5 is a schematic flow chart of apparatus employable in carbon monoxide monitoring of the present invention.

Referring to FIG. 5, the apparatus employed for carbon monoxide determination may be similar to that of FIG. 3 in that a light source 320 which may be white light or ambient light, for example, emits a light beam 322 through optics 324 which may be one or more suitable lens which causes the emerging light beam 330 to impinge on eye 336 thereby causing reflected light 340 to pass through optics 344 which may be one or more lenses and then through filters 350 to cause predominantly the red portion of the spectrum to pass therethrough. The emerging light 354 impinging on a photosensor array 360 converts the received light into responsive corresponding electrical output 364 which in turn is delivered to microprocessor 370. Microprocessor 370 may be any suitably programmed computer which contains information regarding the desired standard ranges for individuals not exposed to undesired levels of carbon monoxide or to the same individual being monitored at another time. In the event that it is determined that a threshold of excessive exposure to carbon monoxide has been exceeded, an alarm signal is emitted over line 372 to alarm 374 which may be any suitable audible, visual or tactile alarm or other alarm. Processor 370 through lead 371 controls the frequency of cycle initiation by controlling light 320.

Figure 6:
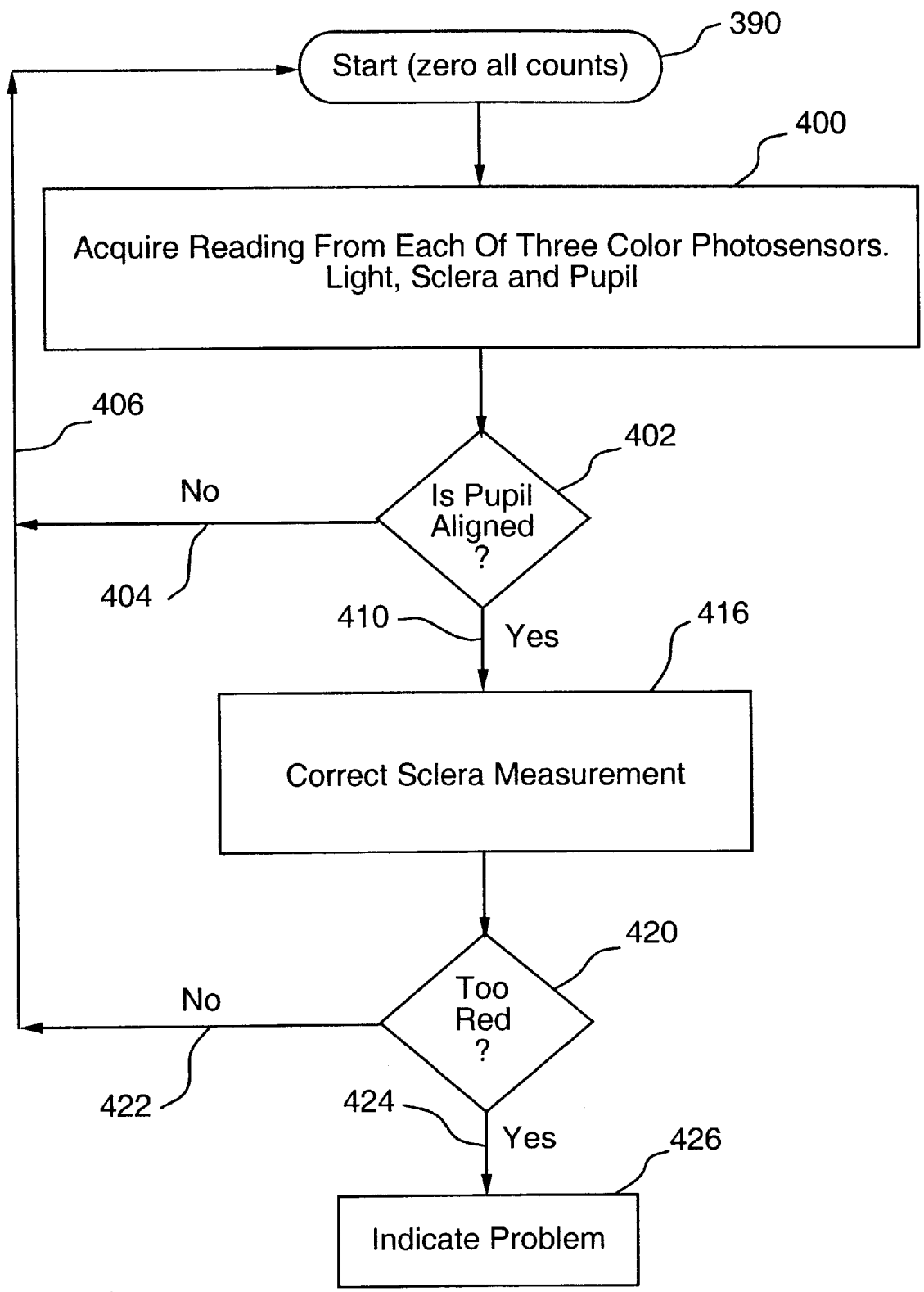
FIG. 6 is a flow chart showing a preferred method of carbon monoxide monitoring of the present invention.

FIG. 6 illustrates a preferred method of the present invention for monitoring the eye for excessive exposure of an individual to carbon monoxide. At the zero level 390, the process is initiated. In this embodiment, three-color photosensors 400 monitoring respectively ambient light which is reflected from the sclera and reflected light from the pupil are provided. A determination is made as to whether the pupil is aligned 402. If the answer is "no," a signal is returned via paths 404, 406 to repeat the cycle. If the answer is "yes" 410, the sclera measurement is adjusted by the light measurement for a more accurate color assessment 416. If it is determined that the red threshold is not exceeded 420, a signal is returned via paths 422, 406 to repeat the cycle at a predetermined interval. If it is determined that the reddening is excessive 424, a suitable alarm 426, which may be audible, visual, tactile or other form is emitted to indicate the existence of a problem.

As in each of the processes, if desired, in addition to issuing or not issuing an alarm, a computer stored record of the inspection cycles with or without enhancement and with or without hard copy output or visual display on a monitor may be employed.

Another version of this device could analyze vasculature in the back of the eye to monitor blood flow, oxygen content and/or the presence of chemicals or gases that would affect the respiratory or cardiovascular systems of the subject. This device could be used to monitor the presence of chemicals or gases. An example could be an indicator for carbon monoxide. It could also be used to measure the oxygen levels in deep-water devices to detect or prevent the onset of nitrogen or oxygen poisoning. These devices could be hat or helmet or helmet/facemask equipped for divers.

Figure 7:
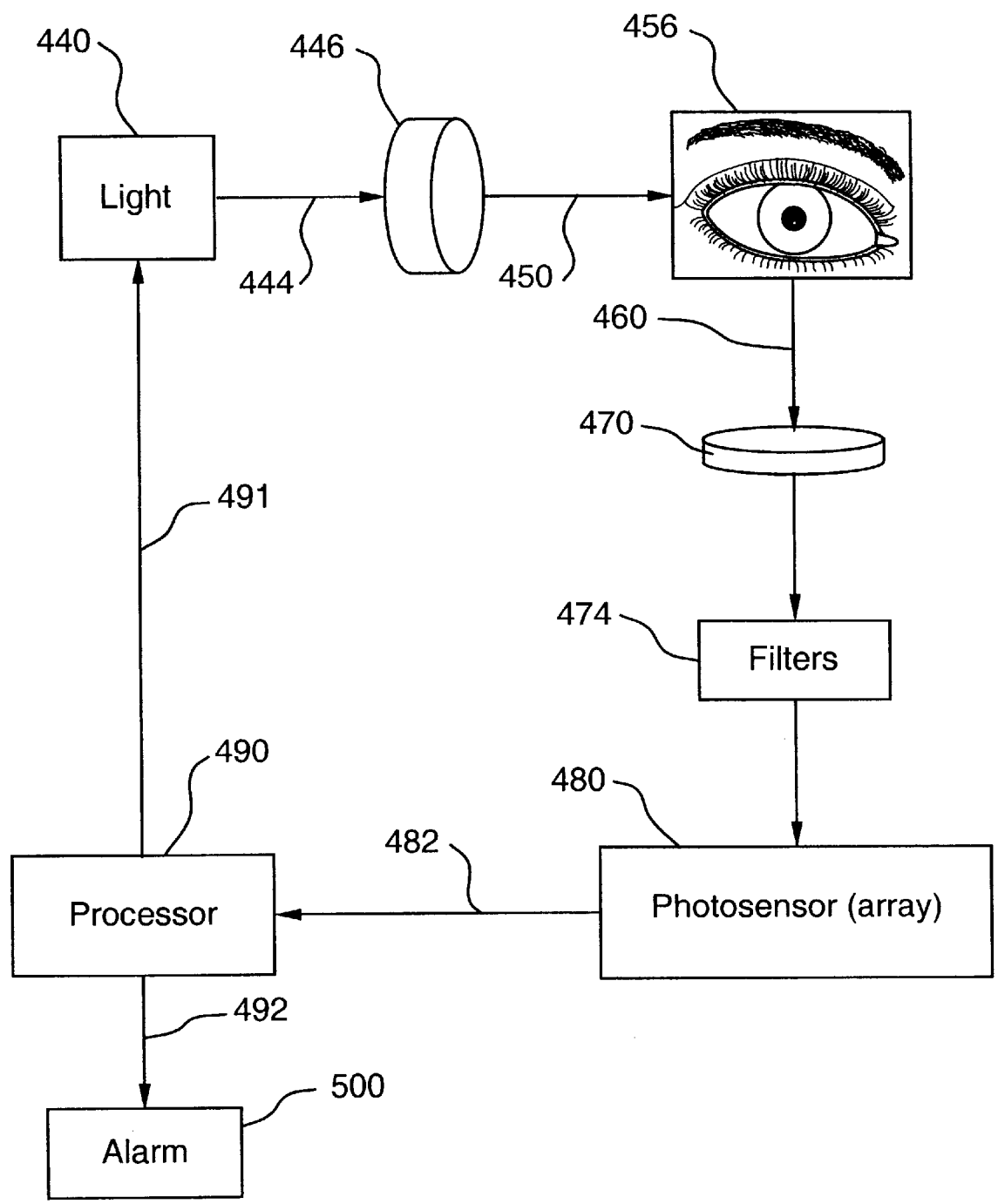
FIG. 7 is a schematic illustration of apparatus employable in a blood or toxin monitoring embodiment of the present invention.

Referring to FIG. 7, apparatus for monitoring blood will be considered. A suitable source of light 440, which may be infrared radiation, creates a light beam 444 which passes through optics 446 which may be one or more converging lenses which cause the light beam 450 to impinge upon the eye 456 with reflected light 460 passing through optics 470 which may be one or more lenses which cause the light to pass through filters 474 and impinge on a photosensor array 480 which may be infrared sensitive and emit responsive corresponding electrical signals to microprocessor 490 which contains stored values of the desired information and effects a comparison therebetween, with an alarm signal 492 being emitted to alarm 500 if the threshold has been exceeded.

Among the preferred sensors 480 for this embodiment are infrared cameras.

Figure 8:
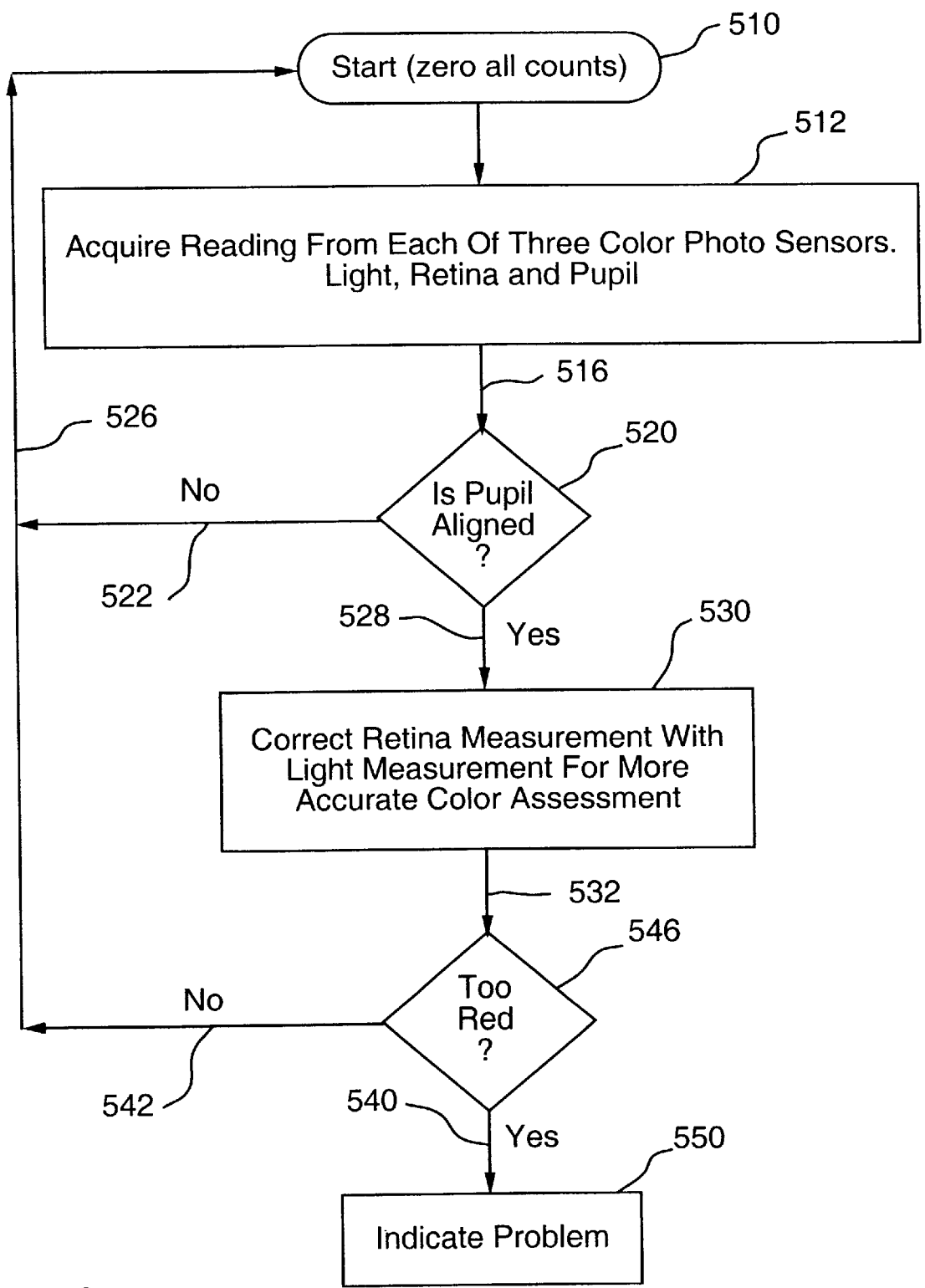
FIG. 8 is a schematic illustration of a method of blood monitoring of the present invention.

Referring to FIG. 8, a preferred method of blood monitoring will be considered. After start 510, information is acquired 512 from each of three-color photosensors which relate, respectively, to light, retina and pupil reflections, the output is passed through lead 516 to the inquiry is pupil aligned 520. If the answer is "no" paths 522, and 526 cause a new cycle to begin. If the answer is "yes" through path 528, the retina measurement is corrected with light measurement for a more accurate color assessment 530. Path 532 responds to the inquiry whether the eye is too red 540 and, if the answer is "no," paths 542, 526 are employed to initiate a further cycle at a predetermined interval. If the answer is "yes" 546, path 540 is employed and an alarm system 550 is activated.

With respect to particular monitoring support and positions for the apparatus of the present invention numerous modes of energizing and communicating with the same will be known to those skilled in the art. To the extent to which that it is to be mounted on head mounted apparel, the system and a source of energizing the same may all be contained within the head mounted apparel with a suitable means for monitoring at least one eye of the user without creating a safety hazard or otherwise interfering with the desired activities of the individual. Mounting such a system has been disclosed, for example, in the product offered by Iscan, Inc. of Burlington, Me. under the general trade designation "HEADHUNTER." Devices may also be mounted in vehicles or in regions adjacent to where the individual will be.

It will be appreciated that for dynamic monitoring, it will generally be preferred to have at least one eye of the individual monitored by the system at frequent predetermined intervals. The frequency of such monitoring will depend to a great extent upon the nature of the activity, the purpose for which monitoring is being initiated, the nature of the characteristic being involved, the degree of the potential health or safety hazard involved, as well as other factors. For miosis and carbon monoxide, it will generally involve a monitoring cycle occurring about every $\frac{1}{60}$ to 30 seconds and preferably about every $\frac{1}{2}$ to 10 seconds. This provides not only frequent data, but also facilitates monitoring trends.

It will be appreciated that the invention may also be employed advantageously to provide for periodic monitoring of patients at intervals of days, weeks, months or years for comparison purposes in order to determine if meaningful changes have occurred over time. For convenience of reference herein, in order to distinguish these longer periods of time from the shorter repeated cycles which may be about $\frac{1}{60}$ to 30 seconds between cycles, such longer periods between monitored cycles will be referred to as "prolonged intervals", and the shorter intervals of less than one hour, will be referred to as "short intervals".

It will be appreciated from the foregoing that the present invention provides an effective means for dynamic monitoring of medical conditions so as to provide indications of potentially hazardous conditions, such as, for example, the embodiments dealing with miosis and carbon monoxide as well as other medical conditions that require attention, such as a blood flow monitoring system.

While for convenience of disclosure herein reference has been made to the human eye, in certain instances advantageous use of the invention may be made on animals, such as guard dogs, or other working animals, for example. All of this has been accomplished in an economical, simple and efficient automated manner.

Whereas particular embodiments of the invention have been described herein for purposes of illustration, it will be evident to those skilled in the art that numerous variations of the details may be made without departing from the invention as defined in the appended claims.

We claim:

1. A method of monitoring a medical condition in a subject comprising
   impinging light on a subject's eye,
   directing reflected light from said impinging light to a photosensor,
   converting said reflected light into corresponding electrical signals by photo sensors,
   delivering said electrical signals to a processor which contains stored information regarding desired parameters for the medical condition,
   effecting a comparison between the photosensor delivered electrical signals and the stored information to determine if an undesirable medical condition exists,
   if such undesirable medical condition exists communicating such event,
   performing said monitoring method without employing external stimuli to alter the position of said eye, and
   mounting apparatus for performing said method in head mounted apparel.

2. The method of claim 1 including cyclically repeating said method.

3. The method of claim 2 including
   repeating said method after a prolonged interval.

4. The method of claim 2 including
   employing said monitoring in blood flow monitoring.

5. The method of claim 2 including
   employing optics to direct said impinging light to said eye and employing optics to direct said reflected light to said photosensors.

6. The method of claim 5 including
   filtering the reflected light emerging from said optics prior to introducing said filtered reflected light to said photosensors.

7. The method of claim 1 including
   repeating said method at short intervals.

8. The method of claim 7 including
   repeating said method on said subject about every $1/60$ to 30 seconds.

9. The method of claim 8 including
   employing said method in miosis monitoring.

10. The method of claim 9 including
    effecting said communication of the presence of an undesired medical condition when the pupil opening is less than a predetermined desired amount, and in such case, issuing an alarm.

11. The method of claim 9 including as part of said method monitoring pupil size.

12. The method of claim 7 including
    employing said method in carbon monoxide monitoring.

13. The method of claim 12 including
    issuing an alarm when said method determines that an undesired medical condition exists through a predetermined amount of carbon monoxide being present in the subject.

14. A method of monitoring a medical condition in a subject comprising
    impinging light on a subject's eye,
    directing reflected light from said impinging light to a photosensor,
    converting said reflected light into corresponding electrical signals by photosensors,
    delivering said electrical signals to a processor which contains stored information regarding desired parameters for the medical condition,
    effecting a comparison between the photosensor delivered electrical signals and the stored information to determine if an undesirable medical condition exists,
    if such undesirable medical condition exists communicating such event,
    performing said monitoring method without employing external stimuli to alter the position of said eye,
    repeating said method at short intervals on said subject about every $1/60$ to 30 seconds,
    employing said method in miosis monitoring,
    effecting said communication of the presence of an undesired medical condition when the pupil opening is less than a predetermined desired amount, and in such case, issuing an alarm, and
    mounting apparatus for performing said method in head mounted apparel.

15. A method of monitoring a medical condition in a subject comprising
    impinging light on a subject's eye,
    directing reflected light from said impinging light to a photosensor,
    converting said reflected light into corresponding electrical signals by photosensors,
    delivering said electrical signals to a processor which contains stored information regarding desired parameters for the medical condition,
    effecting a comparison between the photosensor delivered electrical signals and the stored information to determine if an undesirable medical condition exists,
    if such undesirable medical condition exists communicating such event,
    performing said monitoring method without employing external stimuli to alter the position of said eye,
    repeating said method at short intervals,
    employing said method in carbon monoxide monitoring, and
    mounting apparatus for performing said method in head mounted apparel.

16. A method of monitoring a medical condition in a subject comprising
    impinging light on a subject's eye,
    directing reflected light from said impinging light to a photosensor,
    converting said reflected light into corresponding electrical signals by photosensors, delivering said electrical signals to a processor which contains stored information regarding desired parameters for the medical condition, effecting a comparison between the photosensor delivered electrical signals and the stored information to determine if an undesirable medical condition exists, if such undesirable medical condition exists communicating such event, performing said monitoring method without employing external stimuli to alter the position of said eye, cyclically repeating said method, employing said monitoring in blood flow monitoring, and mounting apparatus for performing said method in head mounted apparel.

17. Apparatus for monitoring a medical condition in a subject comprising a light source for directing light onto at least one eye of said subject without stimulating eye movement, photosensors for receiving reflected light from said eye and converting said light into corresponding electrical signals, a processor for receiving said electrical signals, said processor having stored information regarding desired parameters of said medical condition, and said processor having the capability of effecting a comparison of information obtained from said electrical signals with said stored information and emitting the result of said comparison, wherein said apparatus is mounted at least in part in head mounted apparel.

18. The apparatus of claim 17 including said processor having controls for cyclically repeating said monitoring at predetermined intervals.

19. The apparatus of claim 18 including said processor being structured to repeat said monitoring at short intervals.

20. The apparatus of claim 19 including said processor being structured to repeat said monitoring about every ⅟₆₀ to 30 seconds.

21. The apparatus of claim 18 including said processor having the capability of repeating said monitoring at prolonged intervals.

22. The apparatus of claim 17 including said apparatus being employable in miosis monitoring.

23. The apparatus of claim 22 including said processor having the capability of effecting said emitting the result of said comparison to communicate the presence of an undesired medical condition when the pupil opening is less than a predetermined desired amount, and in such case, issuing an alarm.

24. The apparatus of claim 17 including said apparatus being employable in carbon monoxide monitoring.

25. The apparatus of claim 24 including an alarm being activatable when an undesired medical condition exists through a predetermined amount of carbon monoxide being present in the subject.

26. The apparatus of claim 17 including said apparatus being employable in blood flow monitoring.

27. The apparatus of claim 17 including first optics for directing said light onto said at least one eye and second optics for directing said reflected light to said photosensors.

28. The apparatus of claim 27 including a light filter for filtering the reflected light emerging from said second optics prior to introducing said reflected light to said photosensors.

29. Apparatus for monitoring a medical condition in a subject comprising a light source for directing light onto at least one eye of said subject without stimulating eye movement, photosensors for receiving reflected light from said eye and converting said light into corresponding electrical signals, a processor for receiving said electrical signals, said processor having stored information regarding desired parameters of said medical condition, said processor having the capability of effecting a comparison of information obtained from said electrical signals with said stored information and emitting the result of said comparison, said apparatus being employable in miosis monitoring, said processor having the capability of effecting said emitting the result of said comparison to communicate the presence of an undesired medical condition when the pupil opening is less than a predetermined desired amount, and in such case, issuing an alarm, and mounting said apparatus in head mounted apparel.

30. Apparatus for monitoring a medical condition in a subject comprising a light source for directing light onto at least one eye of said subject without stimulating eye movement, photosensors for receiving reflected light from said eye and converting said light into corresponding electrical signals, a processor for receiving said electrical signals, said processor having stored information regarding desired parameters of said medical condition, said processor having the capability of effecting a comparison of information obtained from said electrical signals with said stored information and emitting the result of said comparison, said apparatus being employable in carbon monoxide monitoring, an alarm being activatable when an undesired medical condition exists through a predetermined amount of carbon monoxide being present in the subject, and said apparatus being mounted at least in part in head mounted apparel.

31. Apparatus for monitoring a medical condition in a subject comprising a light source for directing light onto at least one eye of said subject without stimulating eye movement, photosensors for receiving reflected light from said eye and converting said light into corresponding electrical signals, a processor for receiving said electrical signals, said processor having stored information regarding desired parameters of said medical condition, said processor having the capability of effecting a comparison of information obtained from said electrical signals with said stored information and emitting the result of said comparison, said apparatus being employable in blood flow monitoring, and said apparatus being mounted at least in part in head mounted apparel.

* * * * *